(12) United States Patent
Choi et al.

(10) Patent No.: US 11,085,875 B2
(45) Date of Patent: Aug. 10, 2021

(54) HIGH SPEED IMAGING SYSTEM FOR MEASURING TARGET OBJECT WITHIN SAMPLE

(71) Applicants: Korea University Research and Business Foundation, Seoul (KR); Institute For Basic Science, Daejeon (KR)

(72) Inventors: Won-Shik Choi, Seoul (KR); Moon-Seok Kim, Seoul (KR); Yong-Hyeon Jo, Seoul (KR); Seok-Chan Yoon, Seoul (KR)

(73) Assignees: Korea University Research and Business Foundation, Seoul (KR); Institute For Basic Science, Daejeon (KR)

(*) Notice: Subject to any disclaimer, the term of this patent is extended or adjusted under 35 U.S.C. 154(b) by 0 days.

(21) Appl. No.: 16/591,664

(22) Filed: Oct. 3, 2019

(65) Prior Publication Data
US 2020/0110026 A1  Apr. 9, 2020

(30) Foreign Application Priority Data
Oct. 4, 2018 (KR) .................. 10-2018-0118096

(51) Int. Cl.
*G01B 9/02* (2006.01)
*G01N 21/47* (2006.01)
(Continued)

(52) U.S. Cl.
CPC ..... *G01N 21/4795* (2013.01); *G01B 9/02091* (2013.01); *G01N 33/48* (2013.01); *G02B 21/0048* (2013.01)

(58) Field of Classification Search
CPC ....... G01N 21/4795; G01N 2021/4797; G01B 9/02091; G01B 9/02047; G01B 9/02015; G01B 9/02032; A61B 5/0066
See application file for complete search history.

(56) References Cited

U.S. PATENT DOCUMENTS 9,441,946 B2   9/2016 Massow et al.
2019/0072375 A1* 3/2019 Osawa ............... G01B 9/02091

FOREIGN PATENT DOCUMENTS

| JP | 5629802 B2 | 11/2014 |
| KR | 10-0849193 B1 | 7/2008 |
| KR | 10-1377566 B1 | 3/2014 |

* cited by examiner

*Primary Examiner* — Jonathan M Hansen
(74) *Attorney, Agent, or Firm* — NSIP Law

(57) ABSTRACT

The present invention relates to a high-speed imaging system for measuring a target object within a sample, comprising: a light source emitting a plane wave; an angle-adjustment mirror adjusting an angle of the plane wave emitted from the light source; an optical interferometer dividing the plane wave whose angle was adjusted by the angle-adjustment mirror into a reference wave and a sample wave and forming an interference wave between the reference wave reflected from a reference mirror and the sample wave reflected from the target object; a camera module obtaining the interference wave, and an imaging controller controlling the angle-adjustment mirror to adjust the angle of the plane wave sequentially, forming a time-gated reflection matrix by using the interference waves obtained by the camera module in accordance with each angle of the plane wave, and imaging the target object based on the time-gated reflection matrix.

5 Claims, 13 Drawing Sheets
(11 of 13 Drawing Sheet(s) Filed in Color)

(51) Int. Cl.
*G02B 21/00* (2006.01)
*G01N 33/48* (2006.01)

US 11,085,875 B2

HIGH SPEED IMAGING SYSTEM FOR MEASURING TARGET OBJECT WITHIN SAMPLE

CROSS-REFERENCE TO RELATED APPLICATIONS

This application claims the benefit under 35 USC 119(a) of Korean Patent Application No. 10-2018-0118096 filed on Oct. 4, 2018, in the Korean Intellectual Property Office, the entire disclosure of which is incorporated herein by reference for all purposes.

TECHNICAL FIELD

The present invention relates generally to a high speed imaging system for measuring a target object within a sample. More particularly, the present invention relates to a high speed imaging system for measuring a target object within a sample capable of obtaining a high resolution image of a target object within a medium such as a biological tissue with high measurement speed by using an angle adjustment mirror such as a two-axis Galvanometer scanning mirror.

BACKGROUND ART

Light waves propagating in a biological tissue experience a wavefront distortion due to difference of speed according to refractive index and scattering according to inner structure. This leads to the blurring of an optical focus and the reduction of the resolving power. The wavefront distortion excluding multiple scattering is often called a sample-induced aberration, which manifests itself as a phase retardation of traversing waves depending on their propagation angles. Since the focused spot is a coherent superposition of many angular waves, the sample-induced aberration causes an improper formation of a focus and becomes the source of the focus blurring.

In the past, numerous efforts have been made to compensate the sample-induced aberration in the context of adaptive optics for recovering the diffraction-limit spatial resolution in imaging targets located deep within biological tissues. In typical adaptive optics microscopy, a wavefront sensor is placed at a pupil plane to directly measure angle-dependent phase retardation, which are subsequently compensated by a wavefront shaping device.

This wavefront sensing method requires point particles as guide stars to ensure the proper measurements of the sample-induced aberration. This requirement has been met either by administrating exogenous particles or expressing a fluorescent protein genetically.

In the wavefront sensing method, the light coming from other than the target point source acts as a noise, and the noise increases as the depth of measurement increases. Therefore, multiple iterations have still been necessary to warrant enough signal to noise ratio.

Another widely adopted approach is to iteratively control wavefront shaping devices in such a way to optimize the image intensity or sharpness. While this so-called sensorless approach can work at deeper depth than wavefront sensing approach, it generally takes much longer time due to the need for multiple iterations of wavefront control and image acquisition.

Most of conventional adaptive optics microscopies were designed to work for fluorescence imaging where excitation and emission can easily be separated by their colors. The methods using fluorescence images are highly valuable for biological studies in life science due to their molecular specificity, but their use for the medicine is limited where administrating labeling agents need special care.

Another important issue related to the fluorescence imaging is the speed of the adaptive optics correction operation. Since the fluorescence imaging is an incoherent process, aberration can only be corrected by using physical wavefront shaping devices, not by a post processing.

In most of the developed algorithms, because it is inevitable to take images multiple times to iteratively update aberration correction, the technique for increasing the speed of aberration correction is required, and the speed of aberration correction affects performance of high-depth imaging.

In Korean patent number 10-1688873 "Optical coherence tomography" which is filed by inventors of the present invention and a work by the inventors of the present invention "Imaging deep within a scattering medium using collective accumulation of single-scattered wave (Nature Photonics 9, 253-258, 2015)", a method which was called as CASS (Collective accumulation of single scattering) was proposed.

CASS combines both time-gated detection and spatial input-output correlation. CASS preferentially accumulates single-scattered waves which are the waves scattered only once by the target object, but not at all by the medium. This has resulted in an increase of working depth such that spatial resolution of 1.5 μm can be maintained up to 11 scattering mean free paths.

However, the main limitation comes from the specimen-induced aberration in biological tissues which hinders the accumulation of single-scattered waves. Technically, the achievable depth is even shallower than this fundamental limit by a few scattering mean free paths.

Accordingly, the inventors of the present invention suggested a method which is called as CLASS (Closed-loop accumulation of single scattering) and can simultaneously corrects the scattering and the aberration through a work "High-resolution adaptive optical imaging within thick scattering media using closed-loop accumulation of single scattering (Nature communications volume 8, Article number: 2157, 2017)".

In the CLASS, phase shift of wavefront at each angle is numerically found and corrected, after a time-gated reflection matrix is converted to angular spectrum. The image is optimized by maximizing the intensity of accumulated signal of single scattered waves which is necessary for imaging the target object.

The time-gated hologram imaging method, such as the CASS or the CLASS which is suggested by the inventors of the present invention, uses the interferometer with plane waves, thus obtains interference image between a sample beam and a reference beam. Herein, difference of temporal pulse front between the sample beam and the reference beam is restricted under coherent length of a light source. Thus, when the light source with short coherent length is used for obtaining the detailed time-gated information, only micro-scaled temporal pulse front error is allowed.

In the conventional time-gated hologram imaging method, an angle of an incident wave which is illuminated to the sample is modulated, as shown in FIG. 1 using a spatial light modulator based on liquid crystal for adjusting the temporal pulse front of the sample beam to the temporal pulse front of the reference beam within a range of micrometer scale. Thus, the spatial wavefront of the sample beam can be modulated while the temporal pulse front is maintained. However, a speed for measuring the time-gated reflection matrix is very slow, because the spatial light modulator based on the liquid crystal has a modulation rate about 10 Hz. Thus, in the conventional time-gated hologram imaging method, it is impossible to real-time observing the biological tissue, because the data acquisition time for the time-gated reflection matrix is taken more than 10 minutes.

DISCLOSURE

Technical Problems to be Solved

Accordingly, the present invention is provided to solve the above problems and an object of the present invention is to provide a high-speed imaging system for measuring a target object in a medium such as living tissue at high speed by means of an angle-adjustment mirror such as a two-axis galvanometer scanning mirror instead of a low-speed spatial light modulator.

Technical Solution

The above object is accomplished by a high-speed imaging system for measuring a target object within a sample, comprising: a light source emitting a plane wave; an angle-adjustment mirror adjusting an angle of the plane wave emitted from the light source; an optical interferometer dividing the plane wave whose angle was adjusted by the angle-adjustment mirror into a reference wave and a sample wave and forming an interference wave between the reference wave reflected from a reference mirror and the sample wave reflected from the target object; a camera module obtaining the interference wave, and an imaging controller controlling the angle-adjustment mirror to adjust the angle of the plane wave sequentially, forming a time-gated reflection matrix by using the interference waves obtained by the camera module in accordance with each angle of the plane wave, and imaging the target object based on the time-gated reflection matrix.

Here, the angle-adjustment mirror may comprise a two-axis galvanometer scanning mirror.

Here, the optical interferometer may comprise an off-axis interferometer.

Here, the imaging controller may be configured to generate the time-gated reflection matrix after converting a spectrum of the target object obtained from each interference wave into a spectrum in the laboratory frame which is based on a fixed reference wave whose angle is fixed.

Here, the time-gated reflection matrix may comprise a wave vector of an incident wave which is incident on the sample and a wave vector of a reflection wave which is reflected from the target object; and wherein the imaging controller is configured to execute the following steps: (a) reconstructing the time-gated reflection matrix into an incidence-path aberration-correction matrix which consists of a deviation between the wave vector of the incident wave and the wave vector of the reflection wave, and the wave vector of the incident wave, (b) calculating an optimum incidence-path aberration-correction set which maximizes a total intensity of complex sum of a deviation spectrum between the reflection wave and the incident wave from the incidence-path aberration-correction matrix, (c) correcting the time-gated reflection matrix by using the optimum incidence-path aberration-correction set, (d) reconstructing the time-gated reflection matrix corrected by the step (c) into a reflection-path aberration-correction matrix which consists of the wave vector of the reflection wave, and a deviation between the wave vector of the incident wave and the wave vector of reflection wave, (e) calculating an optimum reflection-path aberration-correction set which maximizes a total intensity of complex sum of a deviation spectrum between a reverse-phase incident wave and a reverse-phase reflection wave from the reflection-path aberration-correction matrix, wherein the deviation spectrum corresponds to the reflection-path aberration-correction matrix, (f) recorrecting the time-gated reflection-matrix by using the optimum reflection-path aberration-correction set, and (g) imaging the target object by accumulating of same reflection wave elements in the time-gated reflection-matrix recorrected by the step (f).

Here, the imaging controller may be configured to repeat the steps (a) to (f) for the recorrected time-gated reflection matrix according to a pre-registered standard, and the step (g) is executed after the repetition of the steps (a) to (f).

The imaging controller may be configured to image the target image by dividing a total view field of the interference wave obtained by the camera module into multiple sub-fields, by generating a time-gated reflection matrix for each sub-field, and by generating images for each sub-field by the execution of the steps (a) to (g) and combining the images.

Effects

According to the above aspects of the present invention, it is possible to provide a high-speed imaging system for measuring a target object in a medium such as living tissue at high speed by means of an angle-adjustment mirror such as a two-axis galvanometer scanning mirror instead of a low-speed spatial light modulator.

BRIEF DESCRIPTION OF DRAWINGS

The patent or application file contains a least one drawing executed in color. Copies of this patent or patent application publication with color drawing(s) will be provided by the Office upon request and payment of the necessary fee."

MODE FOR INVENTION

Hereinafter, exemplary embodiments of the present invention will be described in detail with reference to the accompanying drawings.

Figure 2:
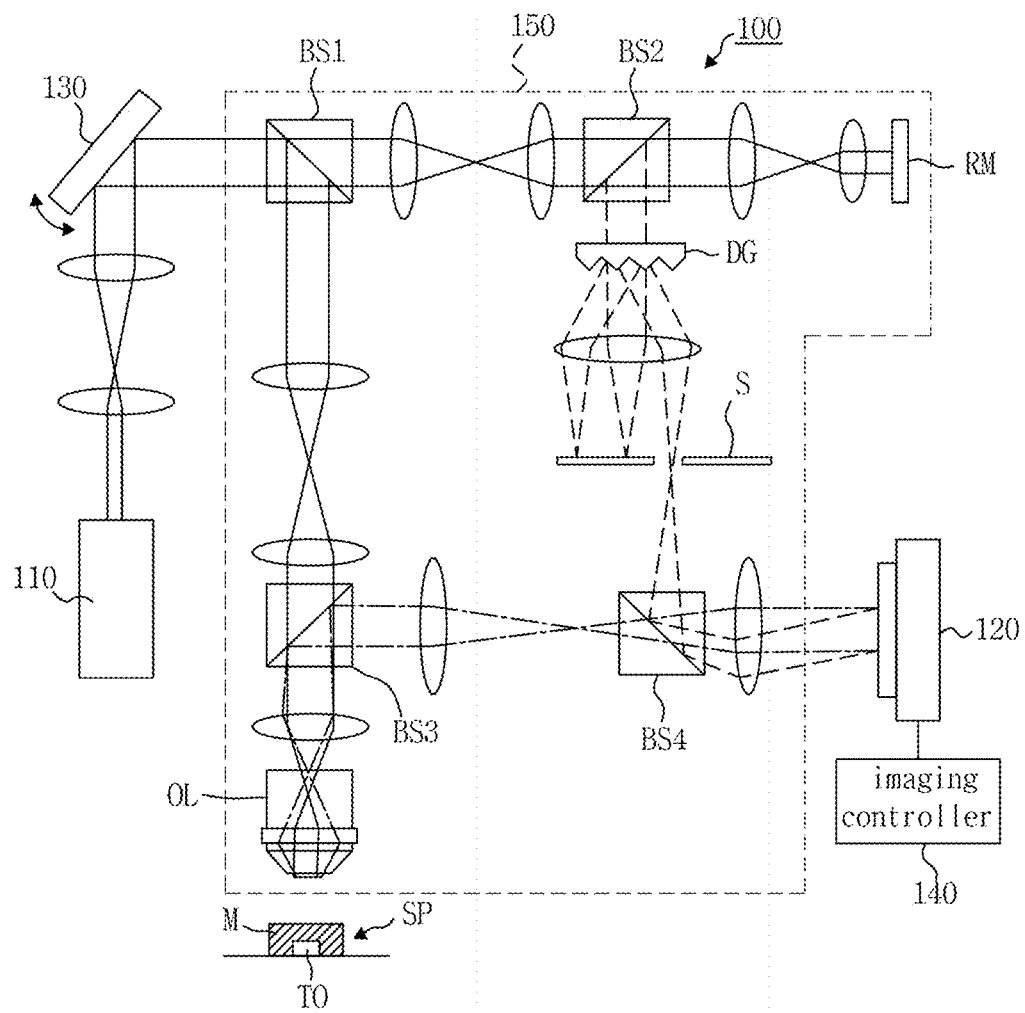
FIG. 2 shows an example of a high-speed imaging system for measuring a target object within a sample according to the present invention.

FIG. 2 shows an example of a high-speed imaging system 100 for measuring a target object TO within a sample SP according to the present invention. Referring to FIG. 2, the high-speed imaging system 100 according to the present invention comprises a light source 110, an angle-adjustment mirror 130, an optical interferometer 150, a camera module 120, and an imaging controller 140.

The light source 110 emits a plane wave to a sample SP having a target object TO within a medium M. In an example of the present invention, as shown in FIG. 2, the light source 110 comprises a laser light source 111 and at least one lens 112, 113.

For example, the laser light source 111 constituting the light source 110 can be a supercontinuum laser and in particular, a Ti-Sapphire femtosecond laser having a center wavelength in the range of about 450 nm to 800 nm can be applied. Laser beam emitted from the laser light source 111 is directed to the angle-adjustment mirror 130 as a plane wave via lenses 112, 113.

The angle-adjustment mirror 130 adjusts an angle of the plane wave emitted from the light source 110. In an example of the present invention, a 2-axis galvanometer scanning mirror is used as an angle-adjustment unit. Compared to a spatial light modulator, the 2-axis galvanometer scanning mirror has a processing speed which is several tens faster.

In the present invention, before the plane wave is split into a sample wave and a reference wave by means of a beam splitter BS1 which will be described hereinafter, i.e., in a state that the mirror is located between the beam splitter BS1 and the light source 110, the angle-adjustment mirror 130 adjusts an angle of the plane wave emitted from the light source 110 and thus, the reference wave split by the beam splitter BS1 also has an adjusted angle.

Figure 1:
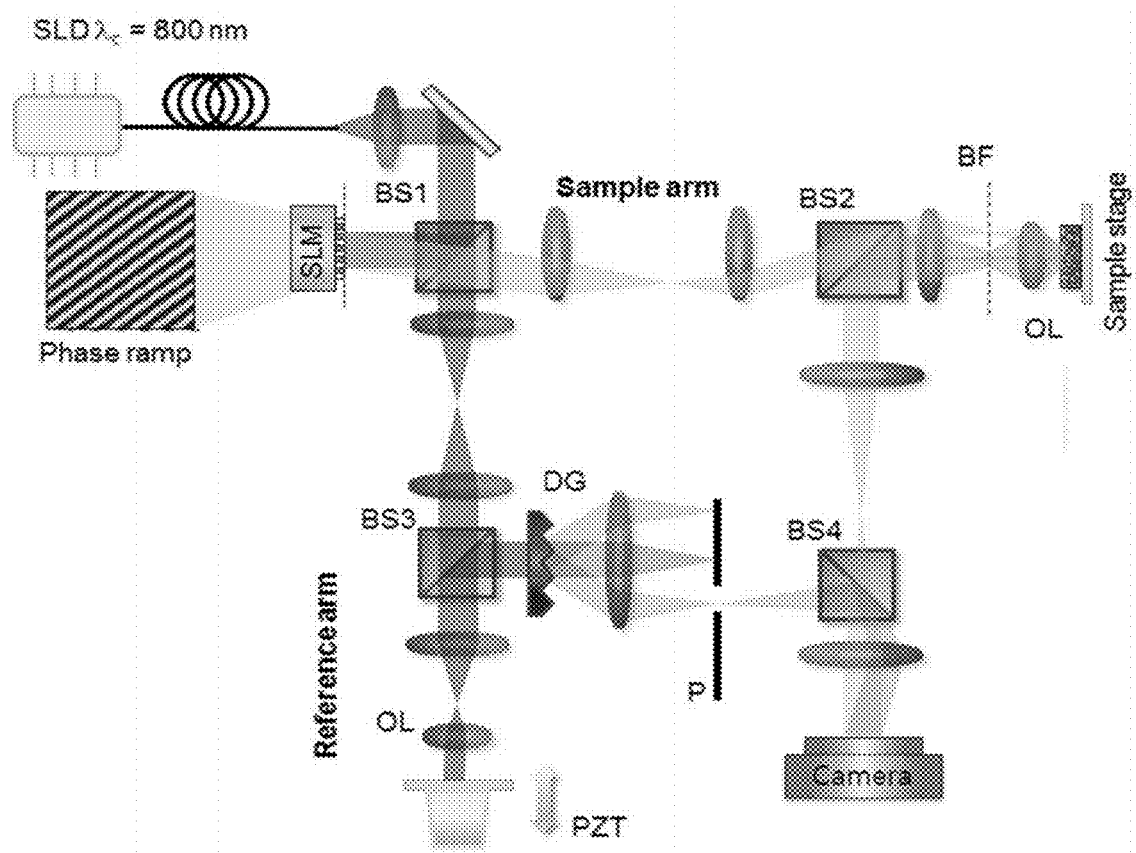
FIG. 1 shows an experimental setup illustrated in Korean patent No. 10-168873.
Figure 3A:
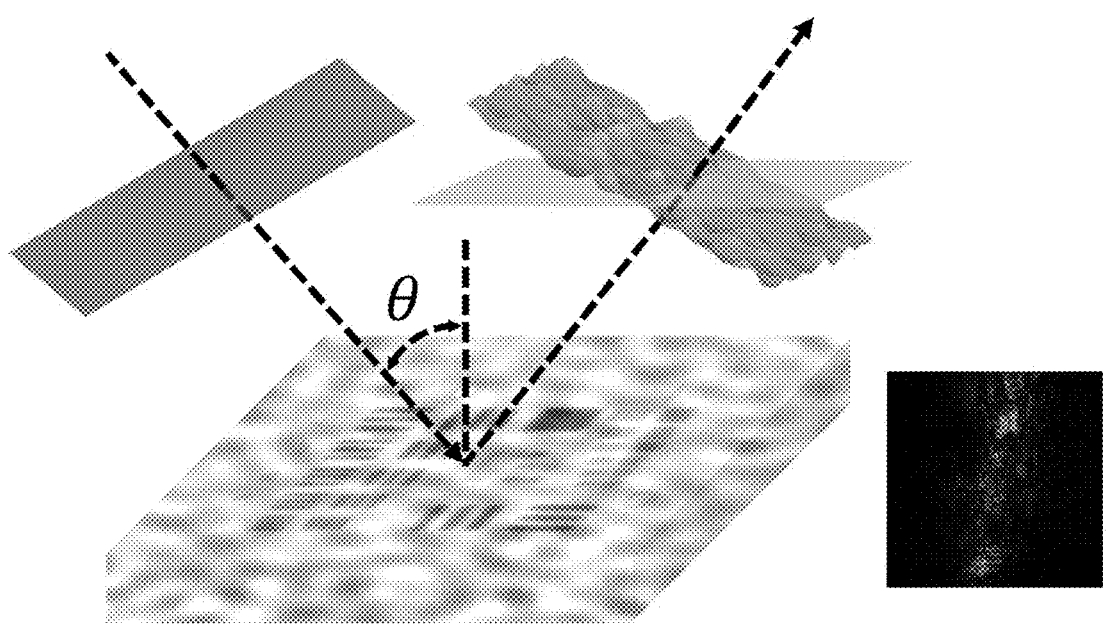
FIG. 3A is a view describing an interference between a reference wave and a sample wave in the ordinary time-gated hologram imaging system.

In case of an ordinary time-gated hologram imaging as shown in FIG. 1, after the split into a reference wave and a sample wave by the beam splitter BS1, only the sample wave experiences the angle adjustment by the spatial light modulator. Such an arrangement is made possible since the spatial light modulator maintains temporal pulse front of the sample wave and changes only wavefront of the sample wave, thereby interference patterns can be created over the entire view field. Meanwhile, if the angle-adjustment mirror 130 is located at the position of the ordinary spatial light modulator of a prior-art time-gated hologram imaging type, the temporal pulse front of the reference wave is changed by the angle-adjustment mirror 130, thereby interference patterns are created in only a partial area, as shown in FIG. 3A.

Figure 3B:
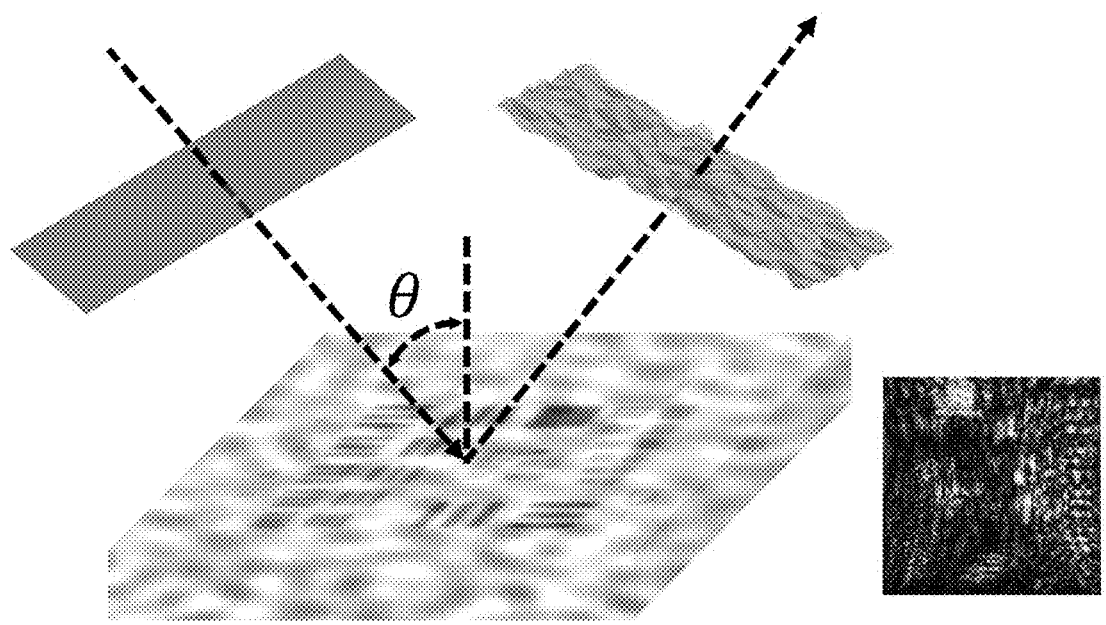
FIG. 3*b* is a view describing an interference between a reference wave and a sample wave in a high-speed imaging system for measuring a target object in a sample according to the present invention.

Therefore, in the embodiment of the invention, the angle-adjustment mirror 130 adjusts an angle before the plane wave from the light source 110 is split into the sample wave and the reference wave and thus, the temporal pulse front of the sample wave is identical to the temporal pulse front of the reference wave as shown in FIG. 3b. Therefore, interference patterns are created over the entire view field in the optical interferometer 150.

Again, referring to FIG. 2, the optical interferometer 150 splits the plane wave whose angle was adjusted by the angle-adjustment mirror 130 into the reference wave and the sample mirror, and gives rise to interference wave by the interference between the reference wave reflected from the reference mirror and the sample wave reflected from the target object TO.

In the embodiment of the invention, an off-axis interferometer is used as the optical interferometer 150 and in FIG. 2, a Mach-Zhender interferometer is applied. Referring to FIG. 2, the plane wave whose angle is adjusted by the angle-adjustment mirror 130 as described above penetrates the beam splitter BS1 to be split into the sample wave and the reference wave.

The reference wave split by the beam splitter BS1 penetrates a beam splitter BS2 and then is reflected by the reference mirror RM. Then, the reference wave is reflected from the beam splitter BS2 and penetrates a diffraction grating DG, so that the first-order diffraction beam moves toward a beam splitter BS4.

Meanwhile, the sample wave split by the beam splitter BS1 penetrates a beam splitter BS3 and then is incident on the sample SP through an object lens OL. The sample wave which was reflected from the sample SP and which therefore has information about the sample SP penetrates the object lens OL and then is reflected from the beam splitter BS3 to move forward the beam splitter BS4.

Then, the sample wave and the reference wave moving toward the beam splitter BS4, respectively, give rise to interference wave by the interference therebetween during the penetration of the beam splitter BS4 and then move toward a camera module 120 such that an interference wave is obtained by the camera module 120.

Here, lenses may be arranged on paths of the sample wave and the reference wave. The arrangement of the optical interferometer 150 as shown in FIG. 2 is one example to embody a high-speed imaging system 100 according to the present invention and thus, the technical spirit of the invention is not limited to the description illustrated in FIG. 2.

The imaging controller 140 is configured to control the angle-adjustment mirror 130 to adjust the angle of the plane wave in sequential order. Also, the imaging controller 140 is configured to create a time-gated reflection matrix using interference wave obtained from the camera module 120 according to plane wave of each angle, and is configured to image a target object TO of the sample SP based on the time-gated reflection matrix.

In the embodiment of the present invention, for example, the imaging controller 140 images a target object TO using a time-gated reflection matrix according to a CLASS (Closed-loop accumulation of single scattering) method described above.

In detail, a time-gated reflection matrix $E_S(\vec{r}^o; \vec{r}^i; \tau_0)$ is constructed from interference waves obtained with regard to the target object TO, i.e. the interference waves obtained by the angle adjustment by means of the angle-adjustment mirror 130. The time-gated reflection matrix contains a complex field map of backscattered wave at the image plane $\vec{r}^o$ for the illumination of a wave at a position $\vec{r}^i$. Here, the flight time $\tau_0$ where temporal gating was applied is set by the position of a reference mirror RM.

Differently from the ordinary interference imaging system as shown in FIG. 1, the high-speed imaging system 100 is configured such that the angle of the reference wave is controlled together with the sample wave as explained above. Let us consider that $E_{in}(\vec{r}, z=0; \vec{k}^i) = E_S^0 \exp[-i\vec{k}^i \cdot \vec{r}]$ is provided for a wave vector $\vec{k}^i$ and a backscattered wave is $E_S(\vec{r}_o; \vec{k}^i, \tau_0)$. Here, $\vec{r}_o$ is a spatial coordinate at the sample plane conjugate to the camera module 120, and $\tau_0$ is a gating time set by a reference mirror.

In the embodiment of the invention, we introduce the reference wave into the camera module 120 according to [Formula 1] to obtain an interferogram given by $I(\vec{r}_o; \vec{k}^i, \tau_0) = |E_S(\vec{r}_o; \vec{k}^i, \tau_0) + E_R(\vec{r}_o)|^2$, with a wave vector $\vec{k}^i / \vec{k}_{DG}$.

$$E_R(\vec{r}_o) = E_R^0 \exp[-i\vec{k}^i \cdot \vec{r}_o - i\vec{k}_{DG} \cdot \vec{r}_o] \quad \text{[Formula 1]}$$

On condition that $|\vec{k}_{DG}|$ is larger than the spatial frequency bandwidth of $E_S(\vec{r}_o; \vec{k}^i, \tau_0)$ (set by the numerical aperture of the objective lens), an interference term in $I(\vec{r}_o; \vec{k}^i, \tau_0)$ by the Hilbert transform of 1 with respect to $\vec{k}_{DG}$ is obtained as follows.

$$E_{GM}(\vec{r}_o; \vec{k}^i, \tau_0) = E_S(\vec{r}_o; \vec{k}^i, \tau_0)(E_R^0 \exp[-i\vec{k}^i \cdot \vec{r}_o])^*$$

$E_{GM}(\vec{r}_o; \vec{k}^i, \tau_0)$ is the complex field map of the backscattered wave in the frame of the rotating reference wave as it contains $(E_R^0 \exp[-i\vec{k}^i \cdot \vec{r}_o])^*$. Here, for the application of CLASS algorithm, we need to extract $E_S(\vec{r}_o; \vec{k}^i, \tau_0)$ which is the complex field map in which the angle of the reference wave was not adjusted.

Figure 4A:
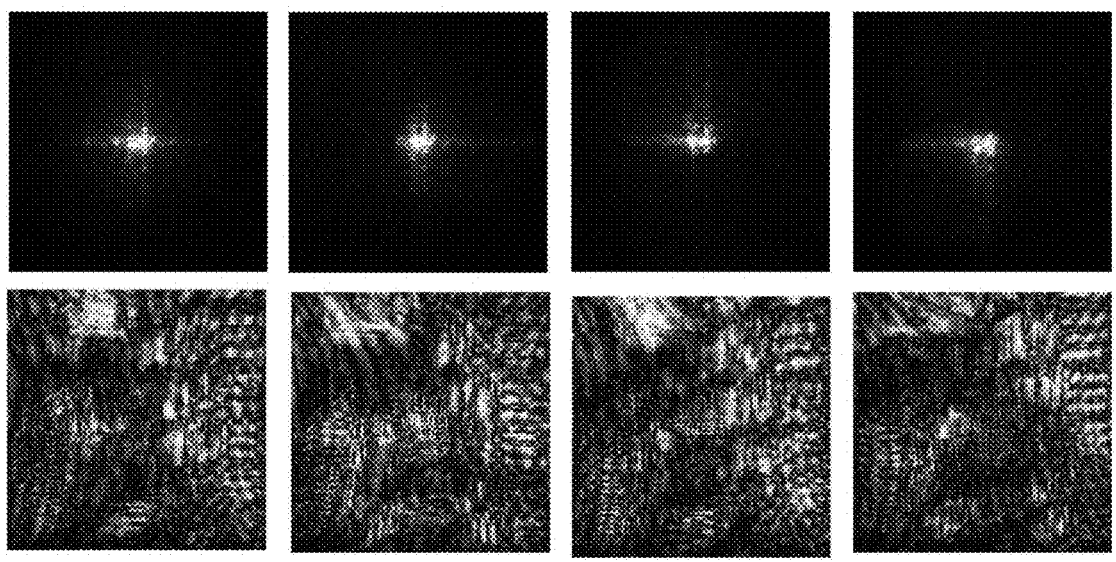
FIG. 4*a* represents hologram spectra per angle obtained by a high-speed imaging system for measuring a target object in a sample according to the present invention, and images obtained by fast Fourier transform of the spectra.

That is, the imaging controller 140 creates a time-gated reflection matrix after transforming the hologram spectrum of each interference wave into a spectrum in the laboratory frame which is based on a fixed reference wave of which the angle is fixed. Images in the upper part of FIG. 4a represent hologram spectrum per angle obtained from the high-speed imaging system 100 according to the present invention. Images in the lower part of FIG. 4a represent images obtained by the fast Fourier transform of the images in the upper part. Also, images in the upper part of FIG. 4b are spectra in the laboratory frame obtained by the transform of hologram spectrum of FIG. 4a based on the fixed reference wave and images in the lower part of FIG. 4b are images obtained by the fast Fourier transform of the spectrum in the laboratory frame.

Figure 4B:
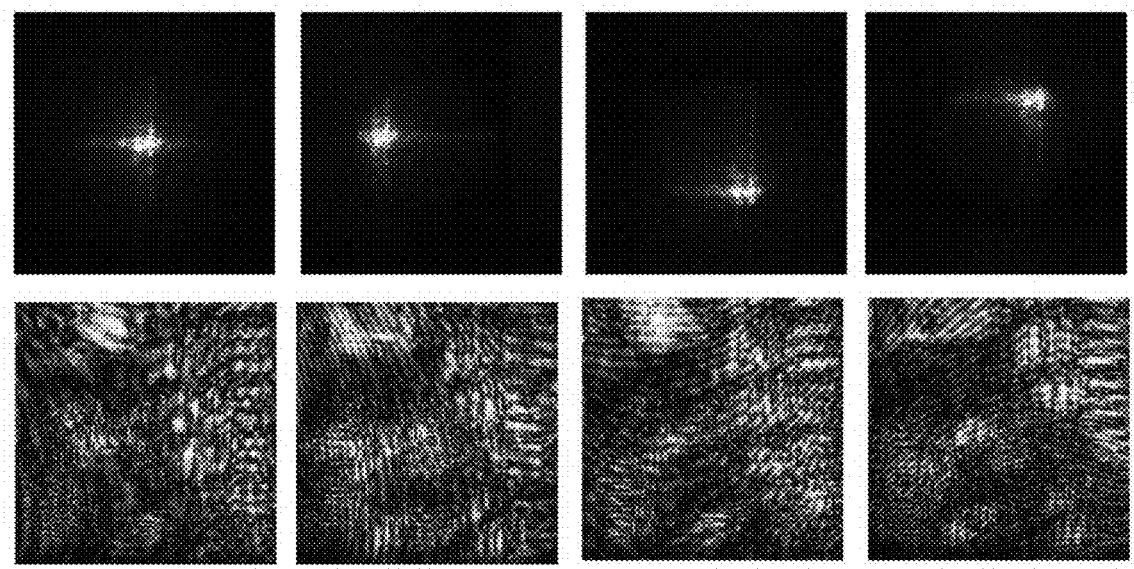
FIG. 4*b* represents spectra in the laboratory frame obtained by transforming hologram spectra based on a fixed reference wave, and images obtained by fast Fourier transform of the spectra in the laboratory frame.

Here, if the images in the lower portion of FIG. 4b are coherently accumulated by the CASS method described above, it is possible to image the target object TO according to the CASS method. In the embodiment of the present invention, a CLASS method by which scattering and aberration can be corrected at the same time is exemplarily applied.

Figure 5:
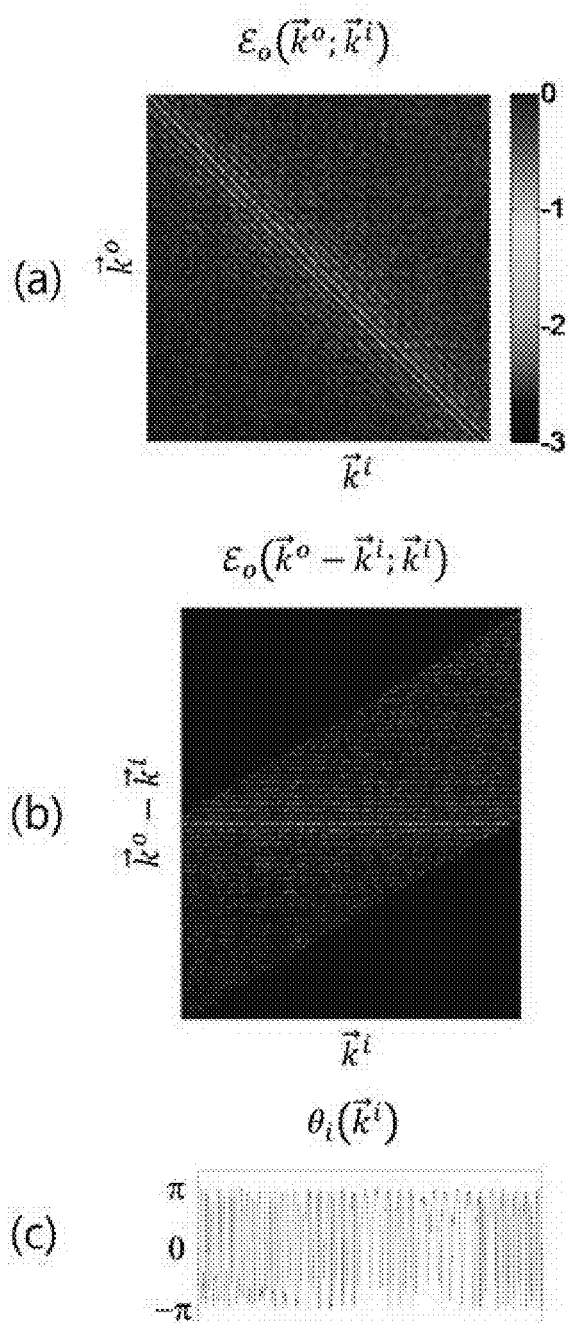
FIGS. 5 and 6 represent each matrix and each aberration correction set in a high-speed imaging system for measuring a target object in a sample according to the present invention.

FIG. 5 (a) shows an example of a time-gated reflection matrix. As shown in FIG. 5 (a), the time-gated reflection matrix consists of a wave vector of incident beam which is incident on the sample SP, i.e., an incident wave vector $\vec{k}^i$ and a wave vector of reflection beam which is reflected from the sample SP, i.e., a reflection wave vector $\vec{k}^o$.

And, the time-gated reflection matrix is reconstructed as an incidence-path aberration-correction matrix. Here, the incidence-path aberration-correction matrix consists of a deviation between the reflection wave vector and the incident wave vector, and the incident wave vector. Then, an optimum incidence-path aberration-correction set $\theta_i(\vec{k}^i)$ at which a total intensity of complex sum of a deviation spectrum $\Delta\vec{k}\bullet$ between the reflection beam and the incidence beam is maximized is calculated from the incidence-path aberration-correction matrix.

If the time-gated reflection matrix is corrected by the calculated optimum incidence-path aberration-correction set, it is possible to correct the aberration caused at the incidence path.

Hereinafter, a process of correcting the aberration which is generated at the incidence path will be explained theoretically.

First, the aberration per angle which is caused at the incidence path is defined as $\phi_i(\vec{k}^i)$, and the incidence-path aberration-correction set for correcting the aberration is defined as $\theta_i(\vec{k}^i)$ as described above.

If an arbitrary incidence-path aberration-correction set $\theta_i^{(1)}(\vec{k}^i)$ is applied to the deviation spectrum $\Delta\vec{k}\bullet$ between the reflection beam and the incidence beam, it can be defined by [Formula 3]. Herein, [Formula 3] can be induced by the description of the above-described paper "High-resolution adaptive optical imaging within thick scattering media using closed-loop accumulation of single scattering (Nature Communications volume 8, Article number: 2157, 2017)", and thus the detailed explanation is omitted.

$$\varepsilon_{CLASS}^{(1)}(\Delta\vec{k}) = \sum_{\vec{k}^i} \varepsilon_o(\vec{k}^i + \Delta\vec{k}) e^{i\theta_i^{(1)}(\vec{k}^i)} \quad \text{[Formula 3]}$$

$$= \sqrt{\gamma}\, O(\Delta\vec{k}) \cdot \sum_{\vec{k}^i} P_i^a(\vec{k}^i) P_o^a(\vec{k}^i + \Delta\vec{k}) e^{i\theta_i^{(1)}(\vec{k}^i)} +$$

$$\sqrt{\beta} \sum_{\vec{k}^i} \varepsilon_o^M(\vec{k}^i + \Delta\vec{k}) e^{i\theta_i^{(1)}(\vec{k}^i)}$$

Then, a set of $\theta_i^{(1)}(\vec{k}^i)$ at which the total intensity of complex sum of deviation spectrum $\Delta k\bullet$ between the reflection beam and the incidence beam is maximized is calculated by [Formula 4], thereby the optimum incidence-path aberration-correction set is calculated.

$$\max_{\theta_i^{(1)}(\vec{k}^i)} \sum_{\Delta\vec{k}} \left|\varepsilon_{CLASS}^{(1)}(\Delta\vec{k})\right|^2 \quad \text{[Formula 4]}$$

In [Formula 4], while an individual $\theta_i^{(1)}(\vec{k}^i)$ is changed from 0 to 2n, a particular value of $\theta_i^{(1)}(\vec{k}^i)$ which maximizes the total intensity of complex sum of the deviation spectrum $\Delta\vec{k}\bullet$ between the reflection beam and the incidence beam is defined as the optimum incidence-path aberration-correction set.

In this regard, it should be noted that only the single-scattered wave plays a part in the above process of maximizing the total intensity of complex sum and the multiple-scattered wave does not play a part. The maps of multiple-scattered wave taken at different incidence angles are uncorrelated with respect to one another, and remained so even after the multiplication of the phase correction. Therefore, the process of maximizing the total intensity of the spectrum of the reflection beam contributes to the aberration correction of the single-scattered wave only.

FIG. 5 (c) shows the optimum incidence-path aberration-correction set calculated by the above process. Herein, for example, in the embodiment of the present invention, after the optimum incidence-path aberration-correction set is applied to the incidence-path aberration-correction matrix, the incidence-path aberration-correction matrix is reconstructed in the form of a time-gated reflection matrix, thereby the aberration of the incidence path of the time-gated reflection matrix is corrected. Here, the optimum incidence-path aberration-correction set is applied to each column of the incidence-path aberration-correction matrix, and the same optimum incidence-path aberration-correction value is applied to one column.

Figure 6:
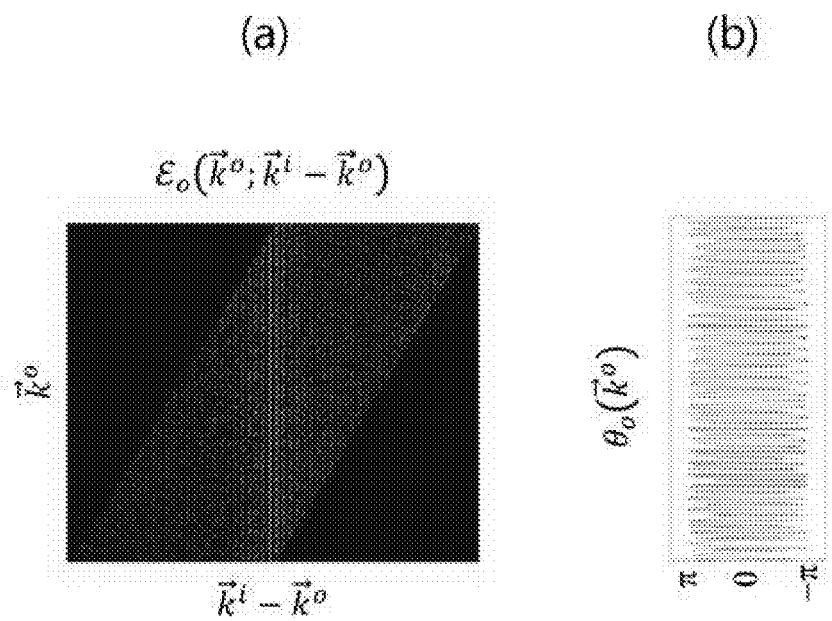

As mentioned above, if the aberration of the incidence path of the time-gated reflection matrix is corrected, the time-gated reflection matrix is reconstructed to a reflection-path aberration-correction matrix. Herein, the reflection-path aberration-correction matrix consists of the reflection wave vector, and a deviation between the incident wave vector and the reflection wave vector, as shown in FIG. 6 (a).

In more detail, the reflection-path aberration-correction matrix represents the change of the incidence beam according to the reflection beam, and it is assumed that the reflection beam is incident on the target object TO as the incidence beam $-\vec{k}^o$, and the incidence beam is detected as the reflection beam $-\vec{k}'^i = -(-\vec{k}^o - \Delta \vec{k})$. Through the above phase conjugation, if an arbitrary reflection-path aberration-correction set $\vec{\theta}_o^{(1)}(\vec{k}^o)$ is applied to a deviation spectrum between the reverse-phase incidence beam and the reverse-phase reflection beam, in which the deviation spectrum corresponds to the reflection-path aberration-correction matrix, the following [Formula 5] is provided.

$$\varepsilon_{CLASS}^{pc}(\Delta \vec{k}) = \qquad [\text{Formula 5}]$$

$$\sqrt{\gamma}\, \mathrm{O}^{-1}(\Delta \vec{k}) \cdot \sum_{\vec{k}^o} p_o^a(\vec{k}^o)^* P_i^{(1)}(\vec{k}^o - \Delta \vec{k})^* \exp i\theta_o^{(1)}(\vec{k}^o) +$$

$$\sqrt{\beta} \sum_{\vec{k}^o} \varepsilon_o^M(\vec{k}^o - \Delta \vec{k})^* \exp\left[i\theta_i^{(1)}(\vec{k}^i)\right] \exp i\theta_o^{(1)}(\vec{k}^o)$$

Then, similar to [Formula 4], an optimum reflection-path aberration-correction set is calculated by calculating $\vec{\theta}_o^{(1)}(\vec{k}^o)$ at which the total intensity of complex sum of deviation spectrum between the reverse-phase reflection beam and the reverse-phase incidence beam is maximized. FIG. 6 (b) represents an example of the calculated optimum reflection-path aberration-correction set as explained above.

Then, the time-gated reflection matrix is corrected again by using the optimum reflection-path aberration-correction set. In an example, after the optimum reflection-path aberration-correction set is applied to the reflection-path aberration-correction matrix, the reflection-path aberration-correction matrix is reconstructed in the form of a time-gated reflection matrix, thereby the aberration of the reflection path is corrected. Here, the optimum reflection-path aberration-correction set is applied to each row of the reflection-path aberration-correction matrix, and the same optimum reflection-path aberration-correction value is applied to one row. Here, in the embodiment of the invention, for example, the above processes of the incidence-path aberration-correction and the reflection-path aberration-correction are repeated according to a pre-registered standard.

If the aberration correction is finished through the above process, a final image is obtained by the accumulation of the same reflection beam elements in the time-gated reflection matrix. Here, the obtaining of image by the accumulation of elements of the reflection beam corresponds to the above mentioned CASS method. That is, the effect caused by the multiple scattering can be eliminated through the accumulation process.

Figure 7:
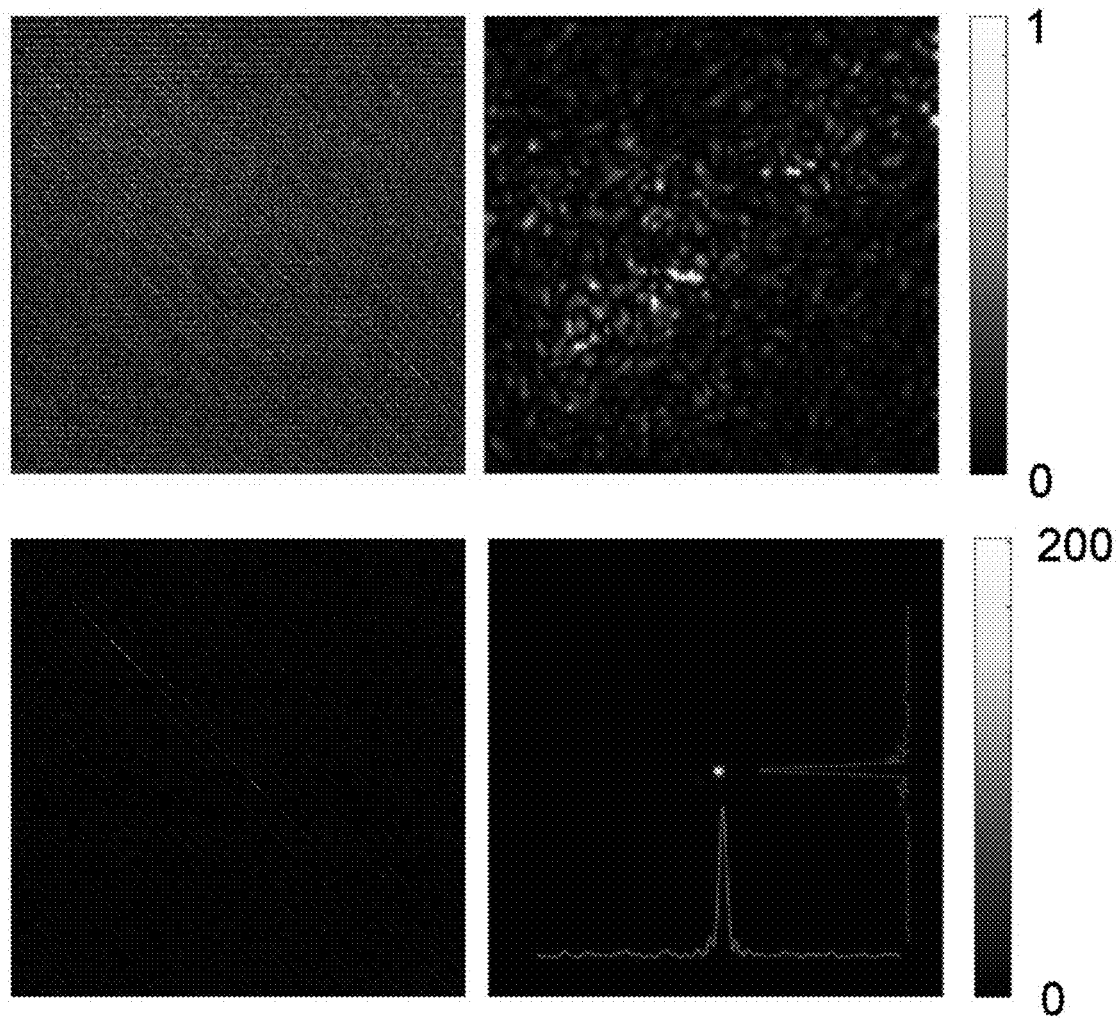
FIGS. 7 to 11 show effects of a high-speed imaging system for measuring a target object in a sample according to the present invention.

Image on the upper left portion of FIG. 7 represents another example of the time-gated reflection matrix in position space. The signals in this matrix are spread out from the diagonal to the off-diagonal elements, which means that measured image is significantly distorted when we illuminate the focused light on the sample (SP), as shown in the image on the upper right portion of FIG. 7. Image on the lower left portion of FIG. 7 represents a time-gated reflection matrix in position space after aberration correction through the above described method and shows that the diagonal elements are distinct. Therefore, when illuminated the focused light on the sample, a clear image can be obtained as shown in the image on the lower right portion of FIG. 7.

Meanwhile, the imaging controller 140 of the high-speed imaging system 100 according to the invention splits the entire view field of interference wave obtained by the camera module 120 into multiple sub-fields and creates time-gated reflection matrix for each sub-field to carry out the above imaging process. Also, the imaging controller 140 combines images for each sub-field to image the target object TO.

Figure 8:
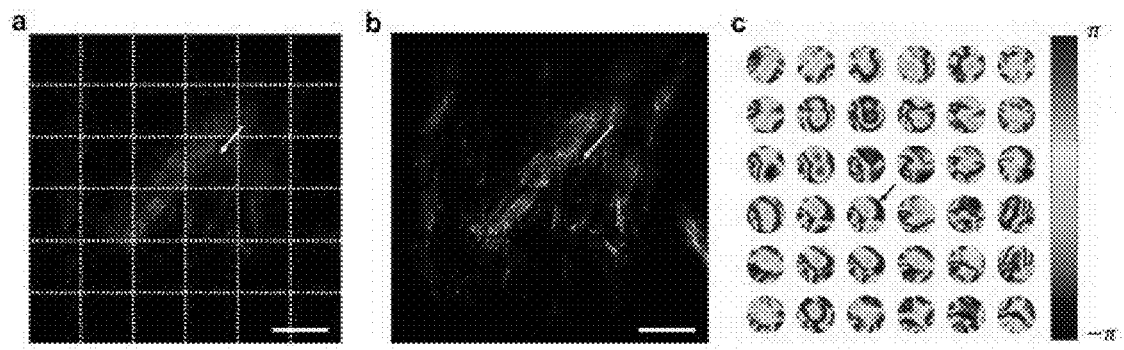

FIG. 8 shows measurements of living Zebrafish by the high-speed imaging system 100 according to the present invention. FIG. 8 (a) is an image before the aberration correction and FIG. 8 (b) is an image having aberration correction by using the high-speed imaging system 100 according to the present invention. In FIG. 8 (b), it is possible to see thin nerve fibers which could not be seen before the aberration correction.

Here, time-gated reflection matrix were created respectively for each of 36 small sub-fields divided by white dotted lines to perform the above described imaging process and FIG. 8 (c) shows aberration-correction sets for each sub-fields obtained by the above process. Imaging processes which are performed respectively for each sub-field are calculated by software and thus can be performed in parallel.

Figure 9:
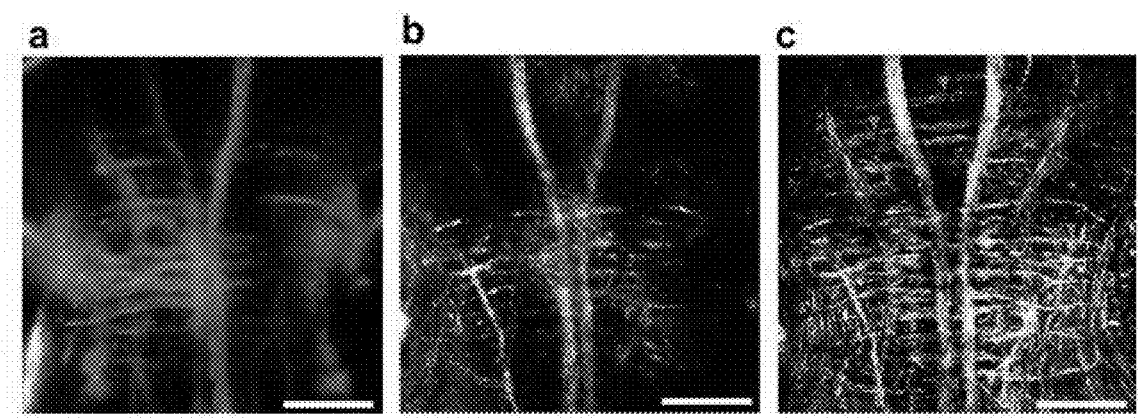

FIG. 9 shows comparison of an ordinary imaging according to the previous method and an imaging according to the high-speed imaging system 100 of the present invention. Images in FIG. 9 used a central nervous system in the hindbrain of living Zebrafish as a sample.

FIG. 9 (a) is an image obtained by using an ordinary confocal fluorescence microscope, FIG. 9 (b) is an image obtained by using a confocal reflection microscope and FIG. 9 (c) is an image obtained by using a high-speed imaging system according to the present invention. In the images obtained by the high-speed imaging system 100 of the invention, strands of nerve fiber which could not be seen by the previous methods can be identified.

Figure 10:
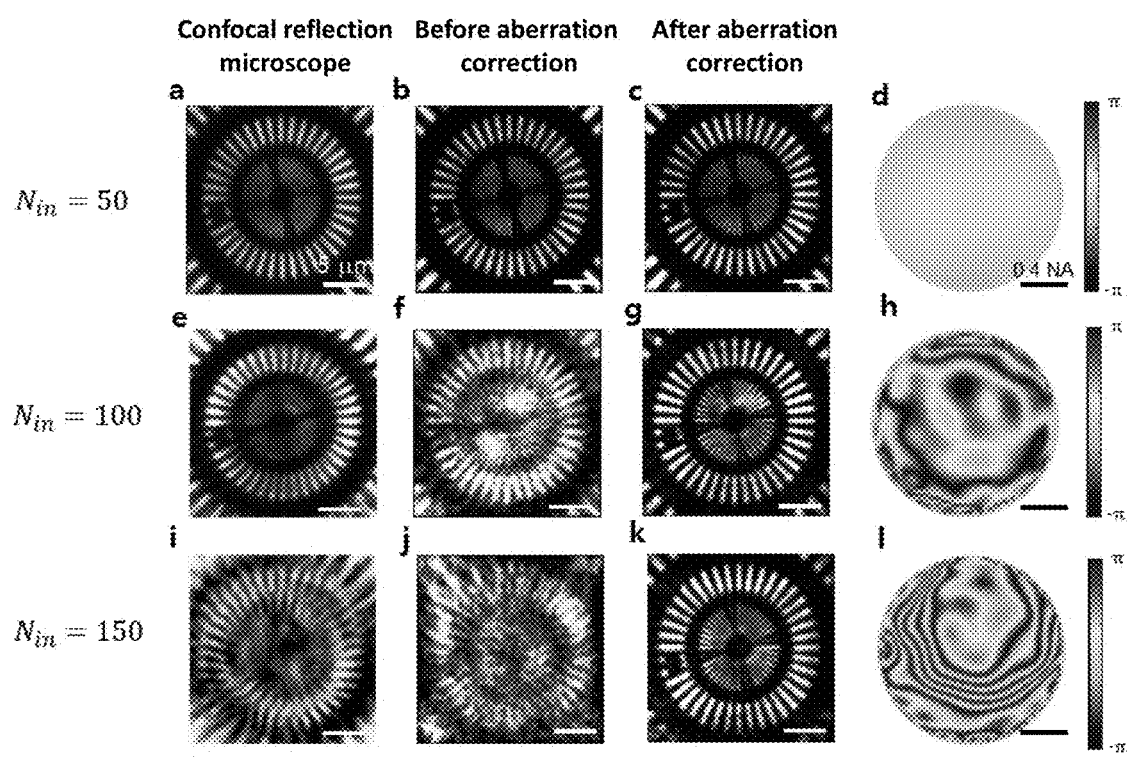
Figure 11:
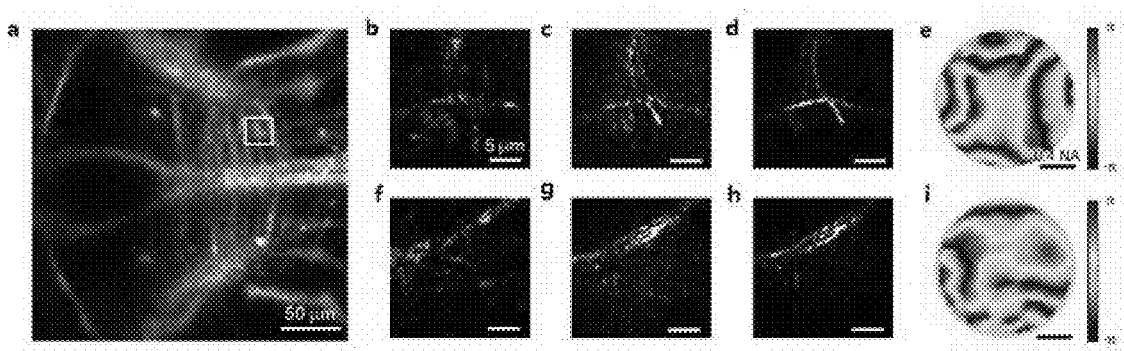

FIGS. 10 and 11 are views explaining the measuring speed of the high-speed imaging system 100 of the present invention. FIG. 10 shows the imaging of a resolution test target to check the speed of measuring the sample according to the present invention.

FIGS. 10 (a), (b), (c) and (d) are images when there is no object which induces aberration on the resolution test target. It is noted that compared to the image (FIG. 10 (a)) obtained by the confocal reflection microscope, both images (FIG. 10 (b)) before the aberration correction and images (FIG. 10 (c)) after the aberration correction in the high-speed imaging system 100 according to the present invention are clear. Here, it took 0.11 second to measure the sample, in particular to obtain 50 holograms per angle.

FIGS. 10 (e), (f), (g) and (h) and FIGS. 10 (i), (j), (k) and (l) represent images when an object inducing an aberration is located on a resolution test target. Compared to FIGS. 10 (e) and (i) which are images obtained by a confocal reflection microscope, FIGS. 10 (f) and (j) which are images before the aberration correction are severely distorted and thus the pattern cannot be resolved. But, after the aberration correction by means of the high-speed imaging system (100) according to the present invention, FIGS. 10 (g) and (k) which are clear images can be obtained and thus, an optical resolution of about 400 nm which is an ideal resolution for an optical system used in the experiment can be identified. FIGS. 10 (h) and (l) represent a complex aberration correction set obtained according to the present invention. In this regard, data acquisition time for a sample for FIG. 10 (g) is 0.22 second and a speed of measuring a sample for FIG. 10 (k) is 0.33 second, which are a time taken for measuring 100 angular holograms and a time taken for measuring 150 angular holograms, respectively.

FIG. 11 represents the measuring speed of the present invention in case of observing a living Zebrafish as a sample. FIG. 11 (a) is an image obtained by an ordinary confocal fluorescence microscope, and images obtained in a white square box correspond to FIGS. 11 (b), (c), (d) and (e) and images obtained in a red square box correspond to FIGS. 11 (f), (g), (h) and (i).

In FIGS. 11 (b) and (f) indicating images obtained by the confocal reflection microscope and FIGS. 11(c) and (g) indicating images before the aberration correction, fiber-structured cranial nerves cannot be identified. But, in FIGS. 11 (d) and (h) indicating images after the aberration correction, fiber-structured cranial nerves are identified clearly. FIGS. 11 (e) and (i) are aberration-correction set for each area. Here, the speed of measuring the sample at each area is 0.5 second and 200 angular holograms were used.

It is understood by those skilled in the art that the foregoing description is a preferred embodiment of the invention but the scope of the invention is not limited to the preferred embodiment, and that various changes and modifications based on the basic concept of the invention defined by the claims are also within the scope of the invention.

BRIEF EXPLANATION OF REFERENCE NUMBER

100: high-speed imaging system
110: light source
111, 112: lens
120: camera module
130: angle-adjustment mirror
140: imaging controller
150: optical interferometer
BS1, BS2, BS3, BS4: beam splitter
OL: objective lens
DG: diffraction grating

The invention claimed is:

1. A high-speed imaging system for measuring a target object within a sample, comprising:
a light source emitting a plane wave;
an angle-adjustment mirror adjusting an angle of the plane wave emitted from the light source;
an optical interferometer dividing the plane wave whose angle was adjusted by the angle-adjustment mirror into a reference wave and a sample wave and forming an interference wave between the reference wave reflected from a reference mirror and the sample wave reflected from the target object;
a camera module obtaining the interference wave; and
an imaging controller controlling the angle-adjustment mirror to adjust the angle of the plane wave sequentially, forming a time-gated reflection matrix by using the interference waves obtained by the camera module in accordance with each angle of the plane wave, and imaging the target object based on the time-gated reflection matrix,
wherein the imaging controller is configured to generate the time-gated reflection matrix after converting a spectrum of the target object obtained from each interference wave into a spectrum in the laboratory frame which is based on a fixed reference wave whose angle is fixed, and
wherein the time-gated reflection matrix comprises a wave vector of an incident wave which is incident on the sample and a wave vector of a reflection wave which is reflected from the target object; and
wherein the imaging controller is configured to execute the following steps:
(a) reconstructing the time-gated reflection matrix into an incidence-path aberration-correction matrix which consists of a deviation between the wave vector of the incident wave and the wave vector of the reflection wave, and the wave vector of the incident wave,
(b) calculating an optimum incidence-path aberration-correction set which maximizes a total intensity of complex sum of a deviation spectrum between the reflection wave and the incident wave from the incidence-path aberration-correction matrix,
(c) correcting the time-gated reflection matrix by using the optimum incidence-path aberration-correction set,
(d) reconstructing the time-gated reflection matrix corrected by the step (c) into a reflection-path aberration-correction matrix which consists of the wave vector of the reflection wave, and a deviation between the wave vector of the incident wave and the wave vector of reflection wave,
(e) calculating an optimum reflection-path aberration-correction set which maximizes a total intensity of complex sum of a deviation spectrum between a reverse-phase incident wave and a reverse-phase reflection wave from the reflection-path aberration-correction matrix, wherein the deviation spectrum corresponds to the reflection-path aberration-correction matrix,
(f) recorrecting the time-gated reflection-matrix by using the optimum reflection-path aberration-correction set, and
(g) imaging the target object by accumulating of same reflection wave elements in the time-gated reflection-matrix recorrected by the step (f).

2. The high-speed imaging system according to claim 1, wherein the angle-adjustment mirror comprises a two-axis galvanometer scanning mirror.

3. The high-speed imaging system according to claim 1, wherein the optical interferometer comprises an off-axis interferometer.

4. The high-speed imaging system according to claim 1, wherein the imaging controller is configured to repeat the steps (a) to (f) for the recorrected time-gated reflection matrix according to a pre-registered standard, and the step (g) is executed after the repetition of the steps (a) to (f).

5. The high-speed imaging system according to claim 1, wherein the imaging controller is configured to image the target image by dividing a total view field of the interference wave obtained by the camera module into a plurality of sub-fields, by generating a time-gated reflection matrix for each sub-field, and by generating images for each sub-field by the execution of the steps (a) to (g) and combining the images.

* * * * *